(12) United States Patent
Dmuschewsky

(10) Patent No.: US 12,734,045 B2
(45) Date of Patent: Sep. 15, 2026

(54) OFFSET SELECTOR

(71) Applicant: WALDEMAR LINK GMBH & CO. KG, Hamburg (DE)

(72) Inventor: Klaus Dmuschewsky, Hamburg (DE)

(73) Assignee: WALDEMAR LINK GMBH & CO. KG, Hamburg (DE)

( * ) Notice: Subject to any disclaimer, the term of this patent is extended or adjusted under 35 U.S.C. 154(b) by 1164 days.

(21) Appl. No.: 17/755,831

(22) PCT Filed: Nov. 19, 2020

(86) PCT No.: PCT/EP2020/082695
§ 371 (c)(1),
(2) Date: May 10, 2022

(87) PCT Pub. No.: WO2021/099472
PCT Pub. Date: May 27, 2021

(65) Prior Publication Data

US 2022/0387188 A1 Dec. 8, 2022

(30) Foreign Application Priority Data

Nov. 19, 2019 (EP) .................................... 19209993

(51) Int. Cl.
*A61B 17/72* (2006.01)
*A61B 90/00* (2016.01)
*A61F 2/46* (2006.01)

(52) U.S. Cl.
CPC ............ *A61F 2/4603* (2013.01); *A61B 90/06* (2016.02); *A61B 2090/061* (2016.02); *A61F 2002/4627* (2013.01)

(58) Field of Classification Search
CPC ........... A61F 2/4603; A61F 2002/4627; A61B 90/06; A61B 2090/061; A61B 17/72
(Continued)

(56) References Cited

U.S. PATENT DOCUMENTS 6,063,091 A * 5/2000 Lombardo ......... A61B 17/1735 606/88
8,491,587 B2 7/2013 McGovern et al.
(Continued)

FOREIGN PATENT DOCUMENTS

WO 2016/183459 A2 11/2016

OTHER PUBLICATIONS

International Search Report and Written Opinion mailed Feb. 17, 2021, in connection with International Patent Application No. PCT/EP2020/082695, filed Nov. 19, 2020, 12 pgs.

*Primary Examiner* — Eduardo C Robert
*Assistant Examiner* — David C Comstock
(74) *Attorney, Agent, or Firm* — Chiesa Shahinian & Giantomasi PC

(57) ABSTRACT

An offset selector for determining an offset between an anchoring section and a joint section of a joint implant component. The offset selector includes a reference portion for determining an offset, a first adjustment device for implementing the offset, and a second adjustment device for adjusting the orientation of the offset to the reference portion. The first and the second adjustment devices are coupled to each other. One of the first adjustment device and a second adjustment device are connected to the reference portion and the other one of the first adjustment device and the second adjustment device is connected to an adjustment portion. The adjustment portion being movable relative to the reference portion.

20 Claims, 3 Drawing Sheets

(58) Field of Classification Search
USPC ........ 606/62, 65, 67, 79, 80, 84, 85, 87, 88, 606/89, 95, 96, 102, 104
See application file for complete search history.

(56) References Cited

U.S. PATENT DOCUMENTS

| | | | | |
|---|---|---|---|---|
| 2008/0177337 | A1* | 7/2008 | McGovern | A61B 17/155 606/86 R |
| 2018/0344333 | A1* | 12/2018 | Dees | A61B 17/1764 |
| 2019/0091028 | A1* | 3/2019 | Bake | A61B 17/1637 |
| 2019/0290291 | A1* | 9/2019 | Collazo | A61B 17/15 |
| 2020/0085592 | A1* | 3/2020 | Oh | A61F 2/4684 |

* cited by examiner

OFFSET SELECTOR

CROSS-REFERENCE TO RELATED APPLICATIONS

This application is a national stage of International Patent Application Serial No. PCT/EP2020/082695, filed Nov. 19, 2020, which claims priority to European Patent Application No. 19209993.5, filed Nov. 19, 2019; the disclosures of all are incorporated herein by reference in their entirety.

TECHNICAL FIELD

The present invention relates to an offset selector for determining and adjusting an offset between an anchorage section and a joint section of a joint implant component and a method for adjusting such an offset.

BACKGROUND OF THE INVENTION

One factor that can significantly influence the success of a joint endoprosthesis is the position and orientation of such an artificial joint in relation to the anatomy of a patient. These parameters are essentially determined during implantation by the preparation of the bone tissue and the selection of the joint components. In case of a long bone, anchoring is usually achieved using an implant stem. For this purpose, a recess is created in the bone tissue that may extend into the medullary canal. A particularly efficient way of creating such a recess is to use a surgical reamer under assistance of a navigation system. As a result, the recess can be precisely placed and formed in the bone tissue by means of a rotary cutting movement. Another method, which is primarily used for anatomically shaped stems of joint replacements, is the use of rasps that are shaped accordingly. Thus, these rasps create a recess in the bone tissue that is adapted to the anatomically shaped stem.

However, during planning and execution of the implantation procedure, it may happen that the placement of the bone recess for optimal anchorage and the placement of the bone recess for optimal anatomical and functional placement of the joint endoprosthesis differ. In such a case, components of a modular implant with an appropriate offset may be used to bring these diverging objectives into alignment for optimal care. Determining and installing the appropriate component, the difference in positioning and orientation between a desired anchorage and a desired functional arrangement of the joint implant can be reconciled.

Although the extent of this offset is already estimated while planning the procedure, the final measurement and, thus, final determination of the offset can often only be carried out during the procedure. At first, the recess in the bone tissue is formed for accommodating the implant stem. Then, the area of the bone tissue close to the joint is prepared for accommodating the joint implant component. The latter preparation is preferably done in view of an appropriate offset to the bone recess for the insertion of the stem that has already been created.

The offset to be determined is particularly composed of two components, namely a radial distance and a relative orientation. Considering the different combinations resulting from these two parameters, many different configurations for a joint replacement and a corresponding number of planning tools for determining these configurations are necessary. If further parameters are taken into account, the number of different configurations multiplies accordingly. Such a parameter is, for example, the stem length. Further, joint replacements generally have different configurations for the right side and the left side of a patient's body.

As a result, the determination of a configuration of a joint implant component continues to be rather difficult. The number of planning tools for this task makes planning and the procedure cumbersome and time-consuming. This also results in an increased need for cleaning and disinfecting before and after the procedure.

SUMMARY OF THE INVENTION

Consequently, it was an objective to provide a device that allows for an easy measurement and adjustment of an offset between an anchoring section and a joint section of a joint implant component. The aim was to enhance the adaptation of a configuration of a joint endoprosthesis to meet the needs of the patient concerning the function of the joint implant component in the patient-specific anatomical environment.

Another objective was to make handling of the device during planning and the surgical procedure easy and efficient. This includes the usability of the device for as many configurations of a joint implant component as possible. Further, the cleaning and disinfection of the device should be facile.

The invention present invention addressing these objectives is defined in the subject matter of the independent claims. Further, the dependent claims define preferred embodiments of the invention.

As a solution, the present provides an offset selector for determining an offset between an anchoring section and a joint section of a joint implant component. The offset selector comprises a reference portion serving as a reference for determining the offset, the offset being defined by a distance and an orientation (angle), a first adjustment device for adjusting the distance to the reference portion, and a second adjustment device for adjusting the orientation about an offset rotary axis relative to the reference portion. The first adjustment device and the second adjustment device are coupled to each other. One of the first adjustment device and the second adjustment device is connected to the reference portion and the other one of the first adjustment device and the second adjustment device is connected to an adjustment portion. The adjustment portion is movable relative to the reference portion by a distance adjustable via the first adjustment device and/or by an angle $\alpha$ djustable via the second adjustment device.

Such an offset selector allows to adjust and, thus, determine both the relative distance and the relative orientation or angle between an anchoring section or reference portion and a joint section or adjustment portion. This may be done for both parameters after the offset selector has been brought into contact with the reference portion. Since no repositioning of the offset selector is required, the offset selector provides accurate results. In other words, errors caused by using different templates for these parameters are basically eliminated.

The reference portion of the offset selector is preferably configured to have a fixed position and orientation relative to the location, where the anchoring section is or will be arranged. In other words, it is preferably configured to fix the position and orientation of the reference portion relative to the anchoring location, in particular a recess in a patient's bone tissue. Thus, the reference portion is to be positioned relative to the patient's bone and is to be held in this position for determining the offset between the anchoring section and the joint section of a joint implant component.

The adjustment of the distance and orientation of the adjustment portion is performed in series. This allows an operator to change the two parameters as desired to determine a combination of subcomponents of a modular joint implant component suitable for the anatomical environment of a patient. As a result, the offset selector comprises at least three bodies that are movable in relation to each other.

In other words, the offset selector is used to adjust an offset between a reference portion and an adjustment portion, thereby bringing the positions and orientations of a joint section and an anchoring section of a joint implant component in line with the anatomy while providing the desired functionality of the joint implant.

The offset selector may be used for both, i.e. for determining the offset and for preparing the implantation site for a joint implant component according to the determined offset. The offset is preferably determined between a point of the reference portion (reference point) and/or a point of the adjustment portion (adjustment point).

The determined offset may then be used to position a tool for preparing the implantation site, for example a tool providing the cutting path for a cutting tool. In this respect, the reference portion and the adjustment portion preferably serve as interfaces, which may be brought into contact to or engagement with a tool or auxiliary device (e.g. a Kirschner wire).

Preferably, the first adjustment device is connected to the reference portion and the second adjustment device is connected to the adjustment portion.

Consequently, the distance that is adjustable by the first adjustment device is defined as being between the reference portion and the second adjustment device, and, thus, the adjustment portion. In particular, the distance is adjustable between a reference point of the reference portion and an adjustment point of the adjustment portion. Preferably, this adjustment point is located along a pivot axis of the second adjustment device in order to adjust the orientation of the adjustment portion. This provides the advantage that the adjustment portion may initially be positioned at a desired distance to the reference portion via the first adjustment device. This makes it easier to adjust the orientation of the adjustment portion relative to the anatomical environment, particularly in case of a visual adjustment. Further, it is possible to iteratively find the offset and the corresponding implant subcomponents that are best suited for the patient.

It is particularly preferred that the reference portion is provided as a tool interface adapted to engage a tool, in particular a tool for preparing an anchoring recess in bone tissue.

This is advantageous since the reference portion may be brought into contact and preferably into engagement with the tool immediately after preparation of the anchoring recess. As a result, a high degree of accuracy in determining the offset can be provided. Also, the number of implantation tools is kept low. In particular, no additional auxiliary device, such as a reference pin, is required for attaching the offset selector to the anchoring recess.

In addition, this configuration of the reference portion has the advantage that the tool interface is commonly the same for every tool in an implantation set, whereas the anchoring recesses created with the tools of an implantation set and their geometries differ from each other. This allows for creating anchoring recesses with different dimensions and/or cross-sections.

The above-mentioned reamers are preferably used for rotationally symmetrical anchoring recesses. Such a reamer generates an anchoring recess that corresponds to the geometry of an anchoring section of a joint implant component. Thus, the reamer is perfectly suited as reference to at least be in contact with the reference portion of the offset selector.

Further, a tool interface generally comprises structural features that allow for an engagement with the offset selector that fixes its relative position and orientation to the tool.

Likewise, it is possible to provide the reference portion with a tool interface in order to engage a rasp. Such a rasp is, for example, used to create recesses in bone tissue for anatomically shaped anchoring sections of joint implants.

The reference portion is preferably formed as a recess. The recess preferably extends throughout the offset selector. Preferably, the recess has a length which is at least 1 times, 2 times or 3 times the maximum width of the recess.

Accordingly, the offset selector may simply be positioned on or attached to a tool via insertion of the tool, in particular the tool interface, into the reference portion. The recess may particularly be a through-hole, making the offset selector independent of the length of the tool section that is inserted. The tool may simply extend through the offset selector. The higher the ratio of the length to the maximum width the more stable and reliable the contact between the offset selector and the tool.

Preferably, the adjustment portion comprises a coupling interface for being coupled to a tool, in particular a cutting guide or a test implant. Even more preferably, the coupling interface is configured to be coupled to the tool in at least two positions and/or orientations.

With this configuration, it is not only possible to determine the offset with the offset selector but also to use it after determining the offset for preparation of the implantation site. Accordingly, there is no repositioning necessary. This enhances accuracy when preparing the bone tissue, the joint implant component will be attached to.

For example, by providing at least two coupling positions/orientations, the offset selector may be applied, for example, to implantation sites on the right and left side of a patient. Another example is to use the offset selector for opposite sides of a joint. For allowing the application of the offset selector to joints of the right and left side of a patient, coupling positions are provided at the coupling interface, which are essentially angularly spaced, in particular by 90° and/or 180°.

Preferably, the first adjustment device and/or the second adjustment device has a latch mechanism which is adapted to adjust the distance or the orientation in steps.

This adjustment in steps, i.e. an adjustment at predetermined distances or angles, has the advantage that the offset may be adjusted and quantified more easily. Further, the modular configurations of a joint implant may be mapped to the adjustment steps of the predetermined distances and/or angles. As a result, the result of a step-by-step adjustment may be used to easily deduce a combination of subcomponents for a modular joint implant component.

Further, the latch mechanism has the advantage that an unintentional adjustment is more reliably prevented. The latch mechanism also provides the user with tactile and/or audible feedback when adjusting the adjustment device.

Preferably, the latch mechanism is a snap body latch mechanism comprising at least two snap bodies, each of the snap bodies acting between an outer body and an inner body and being biased in a radial direction, wherein the inner body is rotatably arranged in the outer body and one of the inner and outer bodies comprises a plurality of snap recesses, the snap bodies being reversibly engageable with the snap recesses. Further, pairs, (i.e. two) of the snap bodies are preferably arranged at diametrically opposed positions in relation to the inner body and outer body.

If the snap bodies are arranged at diametrically opposed positions in relation to the inner and outer body and act between the outer body and the inner body, the biasing of the snap bodies exerts a force acting symmetrically on the inner and/or outer body, thereby preventing jamming or tilting of the inner and outer body relative to one another.

The snap bodies of this preferred embodiment are preferably formed as rotational bodies (i.e. solids of revolution) and even more preferably as spheres. Being formed as rotational bodies has the additional effect that the snap bodies may also act together with the inner body and outer body as a rolling bearing. In other words, having the shape of a rotational body result in the snap bodies supporting the relative position and relative rotation of the outer body and inner body relative to each other as well as the reversible engagement of the rotational bodies.

Preferably, the snap bodies may be brought into and out of engagement synchronously (i.e. reversible engagement) by a corresponding arrangement of the opposite snap recesses. This results in a particularly uniform biasing force acting on the rotary mechanism and preventing the rotary mechanism from jamming. The radial biasing force may be basically caused by an elastic member (e.g. a spring) and/or an elastic deformation of the inner body and/or an elastic deformation of the outer body and/or an elastic deformation of the snap bodies.

If the biasing force is caused by an elastic member, the snap bodies are preferably preloaded by an elastic insert arranged on the inner body of the rotatable bodies, in particular in a recess in the inner circumferential surface of the inner body. Even more preferably, the elastic insert extends along more than half the circumference of the inner body. For example, the elastic insert may be essentially U-shaped.

Consequently, in this embodiment, the elastic member biases the snap bodies and pushes the snap bodies outwards in relation to the rotatable inner and outer bodies. There may be provided one elastic insert per snap body or one elastic insert for a plurality and in particular two snap bodies. The snap bodies are preferably arranged in and guided by snap body recesses of the inner body. The snap body recesses are dimensioned so that each biased snap body is able to project radially outwards relative to the inner body for engaging a snap recess of the outer body.

By arranging the elastic insert in a recess of the inner circumference of the inner body, the elastic insert is held in position to basically prevent any unintentional movement of the elastic insert while applying the preload for biasing that may otherwise interfere with the snap body latch mechanism. If the elastic insert inside the inner body extends over more than half its inner circumference, it also allows the elastic insert to act simultaneously on both snap bodies, thus simplifying the design of the offset selector. As mentioned above, the elastic insert may be basically U-shaped.

The elastic insert preferably comprises in one or both end regions a snap body receiving recess (snap body receptacle) for a partial reception of a snap body. The snap body receiving recess is configured so that the snap body is fixed in its position relative to the elastic member and the elastic member may apply a force to it. Alternatively, the snap bodies and the elastic member may be formed in one piece.

This arrangement of the elastic insert and snap body allows for a reliable assembly of the latch mechanism and a reliable application of the biasing force (preload force) to the snap body.

Furthermore, the latch mechanism may comprise an elastic latch mechanism including an elastic arm, the elastic arm being connected to a first of two bodies and comprising a latching member engageable with an engagement member, wherein the two bodies are movable relative to each other and the second body comprises a plurality of said engaging members.

The two bodies of the elastic latch mechanism are configured to assume different predetermined positions relative to each other. In particular, each of the multiple engagement members represents a predetermined (latching) position, where the latching member is able to engage. The elastic arm is preferably integrally formed with the first body. The elastic arm latch mechanism is a mechanism with a simple configuration that is reliable, durable, easy to clean and easy to disinfect. This latch mechanism also brings the two bodies that are movable relative to each other reliably into engagement at the predetermined (latching) positions defined by the arrangement of the engagement members.

Preferably, one of the first body and the second body, in particular the first body, is mounted to a pivot axis for being pivotable relative to the other one of the first body and second body.

In other words, the movability of the first body and the second body of the elastic arm latch mechanism relative to each other is a relative rotation. The advantage of this pivotable arrangement is a simpler structure than in case of a displaceable arrangement (i.e. linear displaceable arrangement). Nonetheless, the arrangement of the (two outermost) engagement members is configured to allow for an essentially linear displacement. In particular, the engagement members are preferably arranged over an angular range of at maximum 40° and especially at maximum 35°. In other words, the first body and the second body are pivotable in relation of each other over an angular range with a width of 40° and preferably 35°. Further, the engagement members are preferably evenly distributed in such an angular range.

The distance (i.e. radius) between the pivot axis and an engagement position between the latching member and the engaging member is at least 5 mm and even more preferably at least 8 mm. Further, this distance is preferably less than 30 mm or 25 mm for a compact build of the offset selector.

These distances allow for an approximately linear arrangement of the engagement positions between the latching member and the engagement members for determining the offset, i.e. an adjustability from a minimum to a maximum distance between the reference portion and the adjustment portion. In other words, the distance is adjusted along an arc segment that is sufficiently short to determine the distance between the reference portion and the adjustment portion approximately linearly.

The elastic arm preferably includes an actuation portion for disengaging the latching member of the elastic arm.

In particular, the actuation portion is provided at a distal end of the elastic arm. The actuation portion allows for an increase in spring force (i.e. an increase in stiffness of the elastic arm), that keeps the latching member and the engagement member engaged, since a user is able to disengage the elastic arm via this actuation portion. Preferably the size of the actuation portion is configured for an actuation with one finger.

Further, the first body of this embodiment is preferably mounted to the pivot axis. As a result, the actuation portion of the elastic arm may also serve to assist in a relative movement of the first body to the second body between the engagement positions.

Preferably, the first adjustment device and/or the second adjustment device comprises an indicator for indicating the distance or the orientation of the offset.

For a user, the indicator facilitates an adjustment of the offset selector in order to change the distance or orientation as desired, i.e. to reduce or increase the distance or an angle of orientation. Further, after determining the offset with the offset selector, the appropriate joint implant component can be easily selected.

The present invention also provides a method for adjusting an offset between an anchoring section and a joint section of a joint implant component using an offset selector, in particular an offset selector according to any one of the preceding claims, wherein the offset is defined by a distance and an orientation. The method comprises the steps of bringing a reference portion of the offset selector in contact with a first tool, in particular a tool for preparing an anchoring recess in the bone tissue of a patient; bringing a second tool, in particular a trial implant or a cutting guide, into engagement with an adjustment portion of the offset selector; adjusting a distance between the reference portion and the adjustment portion by means of a first adjustment device; and adjusting an orientation between the reference portion and the adjustment portion by means of a second adjustment device. The reference portion and the adjustment portion are coupled in series via the first adjustment device and the second adjustment device.

The determination of the distance and orientation is performed with one and the same offset selector. This offset selector is placed directly at a tool (i.e. is brought into contact and is preferably engaged with the tool), wherein the tool is preferably for preparing the implantation site for the anchoring section in the bone tissue of a patient. Accordingly, the offset selector allows for determining the offset between an anchoring section and a joint section in an easy and quick manner as well as with a high accuracy. In addition, it is possible to directly use the offset determined and adjusted by the offset selector to prepare the implantation site further, in particular the bone tissue, where the joint section is to be placed. For this, a tool may be used that is preferably attachable to the offset selector, in particular a cutting guide.

BRIEF DESCRIPTION OF THE DRAWINGS

The following figures illustrate preferred embodiments. These embodiments are not to be construed as limiting but are merely for enhancing the understanding of the invention in context with the description. In these figures, same or corresponding reference signs refer to features throughout the figures that have the same or an equivalent function and/or structure.

DETAILED DESCRIPTION OF PREFERRED EMBODIMENTS

Figure 1:
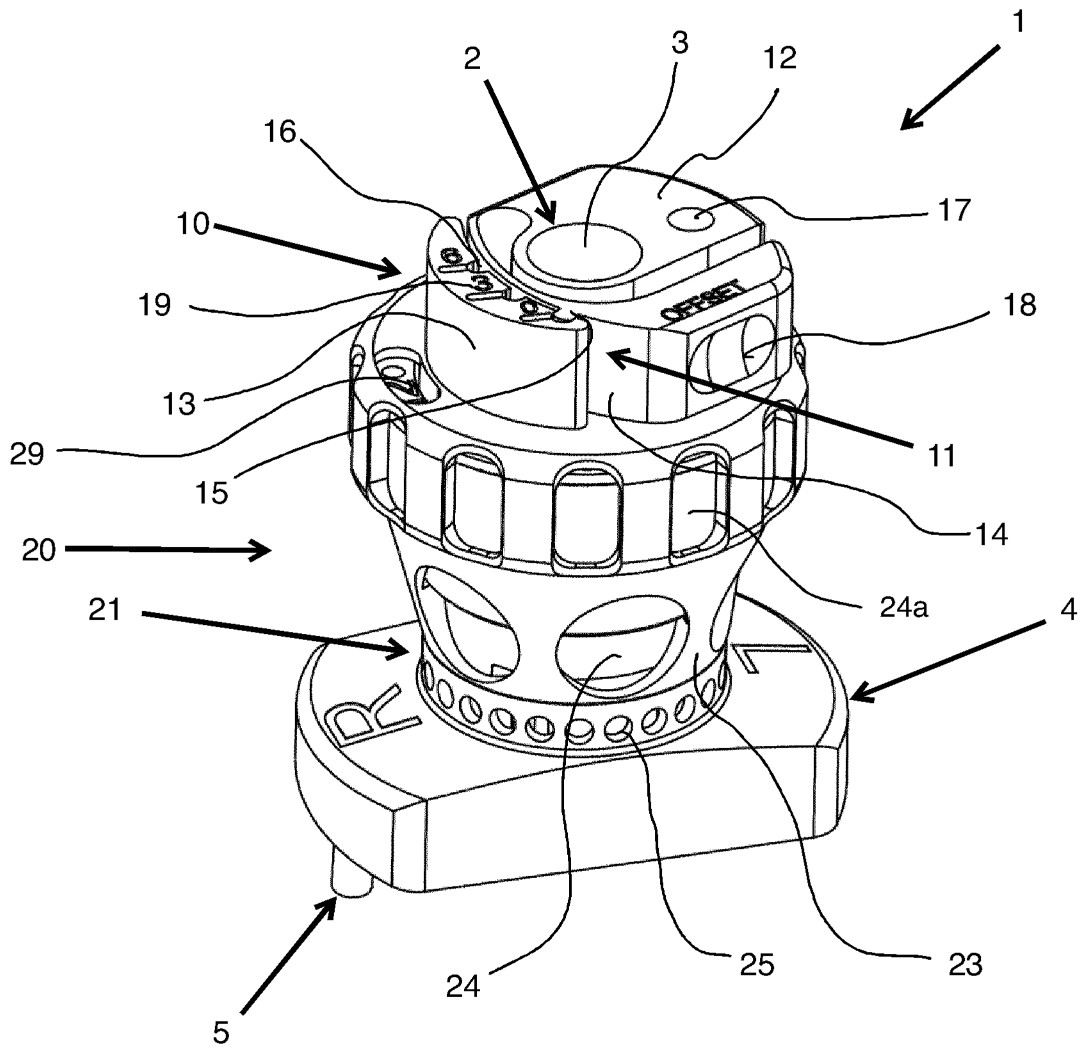
FIG. 1 is a three-dimensional view which illustrates an exemplary embodiment of an offset selector in accordance with this disclosure.

FIG. 1 illustrates an exemplary embodiment of an offset selector 1 configured for an adjustment of an offset between a reference portion 2 and an adjustment portion 4, which simulates the offset between an anchoring section and a joint section of a joint implant component (not shown). The offset may be determined by adjusting a distance A and an orientation α by means of an adjustment device 10 and an adjustment device 20, respectively, described in more detail further below. In this way, an offset can be determined for the joint implant component that is anatomically and functionally adapted to the patient. Based on the determined values of the offset, it the selection of the joint implant components suitable for the implantation site is facilitated.

As described in more detail below, once the offset has been determined, the offset selector 1 may also be used to place a tool at the offset selector, in particular at the adjustment portion, to prepare the bone tissue at an implantation site for receiving the joint section of the joint implant. The tool may be, for example, a cutting guide (not shown).

The offset selector 1 shown in FIG. 1 has a reference portion 2, a first adjustment device 10, a second adjustment device 20 and an adjustment portion 4. The reference portion 2 is intended for positioning the offset selector 1 at a predefined position relative to a bone. The predefined position is preferably an anchoring position of a joint implant component. After placement, an offset between an anchoring section and a joint section may then be adjusted and determined.

In particular, reference portion 2 is used to establish a relationship between an area, where the joint section of a joint implant component should be located, and an area, where the anchoring section of a joint implant component should be implanted. The offset selector 1 is preferably placed by attaching the reference portion 2 to a tool for preparing the anchoring site for a joint implant component or to a tool for testing, such as a trial implant.

As described above, the preparation of the anchoring site may comprise forming a recess in the bone tissue adjacent to the joint implant component to be implanted. For example, a reamer or rasp may be used. Since the bone tissue is prepared with these tools to accommodate the anchoring section, these tools are basically arranged in the bone tissue similar or like the anchoring section to be implanted. As a result, such tools may be advantageously used to place the reference portion 2 of the offset selector 1 after at least partly preparing the bone tissue. Thus, the reference portion 2 is preferably configured to be coupled to the interface of such a tool.

In the exemplary embodiment of an offset selector 1 shown in the figures, the reference portion 2 comprises a tool recess 3 that is preferably adapted to such an interface of a tool. More specifically, the tool recess 3 may be configured so that it is possible to place the offset selector 1 at or onto a tool interface. This preferably includes structural features which engage the offset selector 1 at least in the direction of rotation about an axis of rotation, in particular by employing a positive fit (or form fit) and/or friction fit. The axis of rotation is preferably arranged parallel to the offset rotary axis VA of the second adjustment device 20 for adjusting the orientation of the adjustment portion 4. Such structural engagement features are provided, for example, in a tool interface of a reamer. These features of a tool interface enable a transfer of a movement, such as a rotational movement, for carrying out a cutting motion.

Preferably, the tool recess 3 is configured as a through hole. This allows the offset selector 1 to have a compact shape, as a section of a tool, in particular a tool interface, may extend through the tool recess 3. As a result, the offset selector 1 may be configured to be shorter than a tool interface and, thus, more compact.

Figure 4:
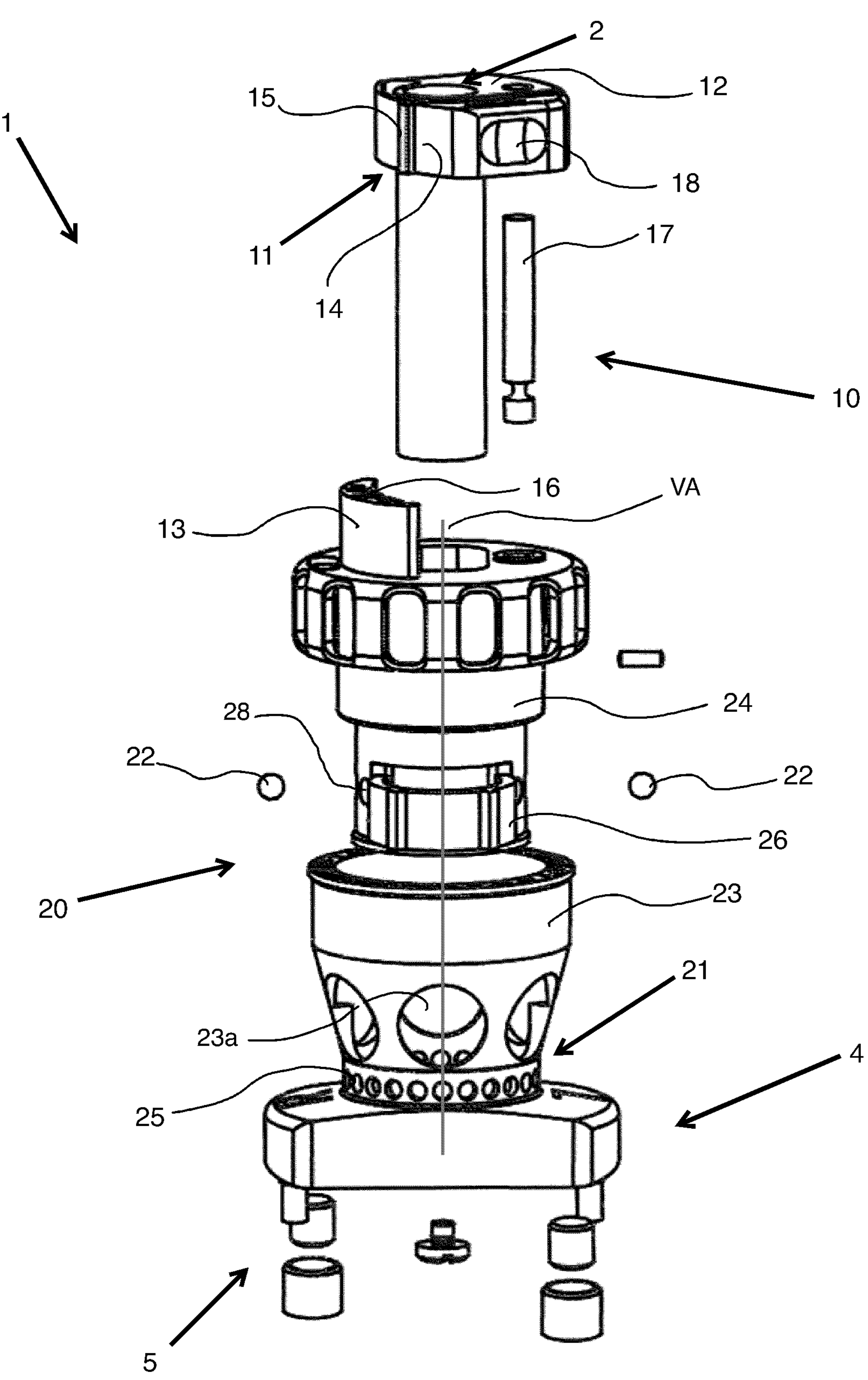
FIG. 4 is an exploded view of the offset selector shown in FIGS. 1 to 3.

As already described above, the dimensions of the tool recess 3 are preferably chosen so that the length of the tool recess 3 is greater than the maximum width of its cross section (cf. FIG. 4). This will have a stabilizing effect on the angular position of the offset selector 1 about an axis perpendicular to the length of the tool recess 3.

Figures 2, 3:
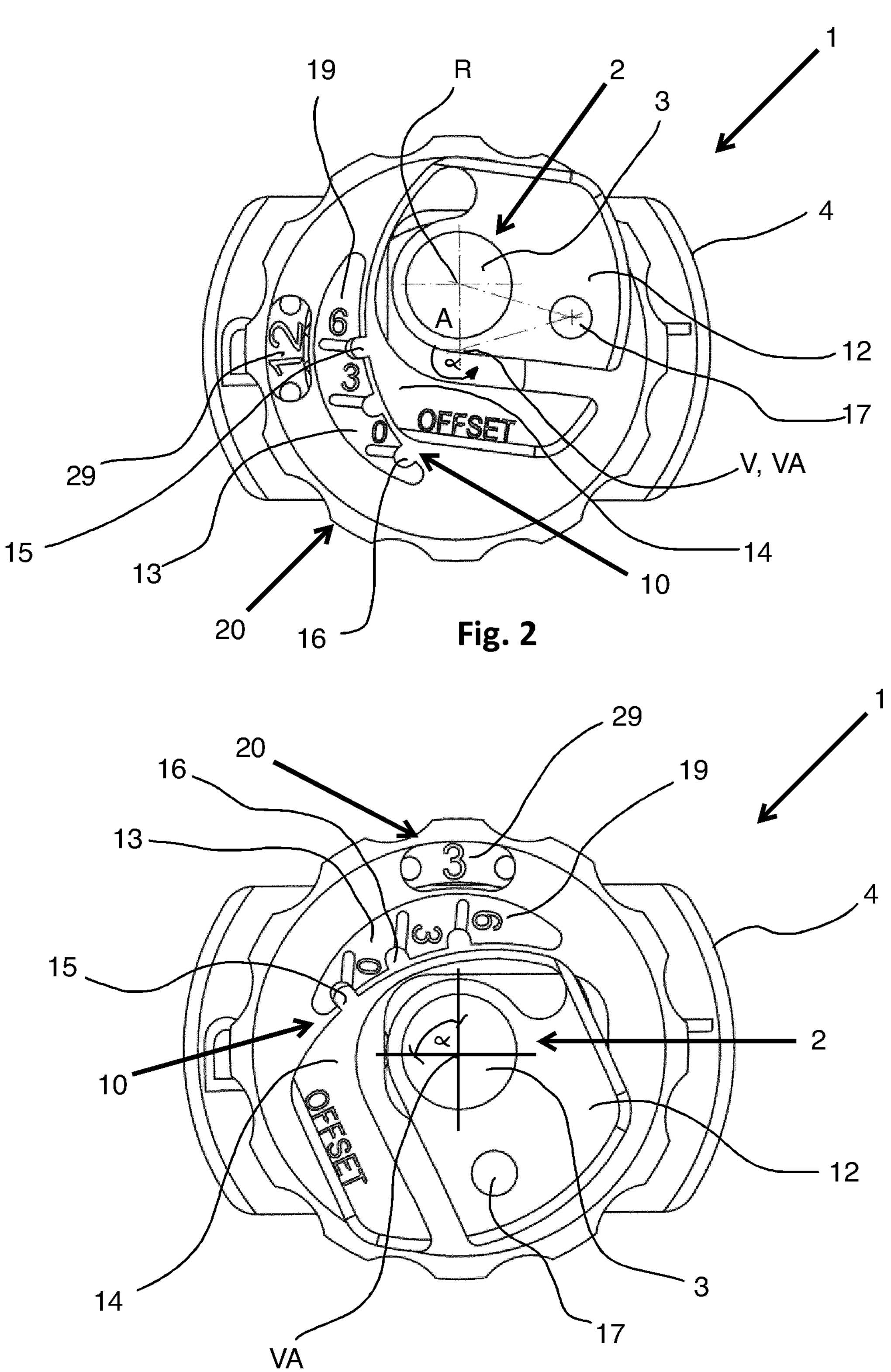
FIG. 2 is a plan view of the offset selector of FIG. 1, wherein the offset selector is adjusted to an exemplary offset.
FIG. 3 is a plan view of the offset selector of FIG. 1, wherein the offset selector is adjusted to another exemplary offset which is different from the offset shown in FIG. 2.

The offset adjustable by the offset selector 1 is set between the reference portion 2 and the adjustment portion 4 and includes a distance A and an orientation angle α (see FIGS. 2 and 3). The adjustment portion 4 is offset relative to the reference portion 2 by adjusting the first adjustment device 10 and the second adjustment device 20. This offset corresponds to or simulates an offset between the anchoring section and the joint section of a joint implant component.

For facilitating an adjustment of the offset or a subsequent preparation of bone tissue, the adjustment portion preferably includes a coupling interface 5. This coupling interface 5 may, for example, be configured to be coupled with a tool that assists visually in an adjustment of the offset. For example, a template may be used to visually highlight the position of the adjustment portion 4 relative to anatomical surroundings and, thus, to assist during an adjustment of the offset.

Further, a tool that supports further processing of the bone tissue may be engaged with the coupling interface 5. Preferably, such a tool is a cutting guide. Such a cutting guide may also include the previously described function of a template for facilitating the recognition of the position of the adjustment portion 4 relative to anatomical surroundings.

Additionally or alternatively, the geometry of the adjustment portion 4 may be configured to assist in an adjustment of the offset. More specifically, the shape of the adjustment portion 4 may be configured so that it assists in a visual alignment of the adjustment portion 4 relative to the anatomical environment.

Further, it is possible that the adjustment portion 4 comprises a cutting guide (not shown). Nonetheless, the adjustment portion 4 preferably includes a coupling interface that is at least also configured for mounting a cutting guide.

The adjustment portion 4 may be configured to allow further adjustments in addition to an adjustment of the offset in order to support the functionality of an anchoring section and a joint section of a joint implant component. In particular, the coupling interface 5 may be configured for mounting a tool in several and preferably 2, 3 or 4 positions. In case of the embodiment shown in FIG. 1, this is, for example, indicated by the inscriptions L and R, i.e. left and right. In particular, this label indicates to a user the position and/or orientation for a tool to be coupled to the coupling interface 5 taking into account the anatomy of the patient. In other words, such a label may indicate the orientation in which the tool for a joint on the left or right side of a patient's body should be attached. It is also possible to provide such indications for the attachment of tools for opposing and interacting joint implant components.

As an alternative or an addition to the coupling interface 5, the reference portion 2 may also be configured in this way. All these embodiments and modifications provide the offset selector with additional adjustment possibilities. This has the advantage that the number of instruments or tools that have to be provided can be reduced.

As described above, for the offset selector 1 shown in the figures, the first adjustment device 10 for adjusting the distance and the second adjustment device 20 for adjusting the orientation are connected in series between the reference portion 2 and the adjustment portion 4 in this order. Consequently, the distance A of the offset is adjusted relative to the reference portion 2 via the first adjustment device 10. After an adjustment of the distance A, this causes the second adjustment device 20 and the adjustment portion 4 to be spaced apart from the reference portion 2 by this distance A during an adjustment of the orientation about the offset rotary axis VA. In other words, the offset rotary axis VA, which preferably extends substantially perpendicular to an offset plane, is at a distance A from a reference point R of reference portion 2 in that offset plane.

This is illustrated in FIGS. 2 and 3 by top views of the offset selector 1. In FIG. 2, a distance A is indicated, which has been adjusted between the reference portion 2 or a reference point R thereof and the adjustment portion 4 or an adjustment point V thereof. In other words, the second adjustment device 20 has been offset by the distance A. The distance that has been adjusted is preferably communicated to a user via a distance indicator 19. The distance indicator 19 may be provided as a measurement, as in this example. Nonetheless, other distance indicators 19 are conceivable, such as distance indicator using categorical distances (e.g. 1, 2, 3 . . . or A, B, C).

Preferably after setting a distance A, the second adjustment device 20 may be used to adjust an orientation angle α. An orientation indicator 29 preferably indicates the value of the orientation angle α to a user. In the example shown, orientation indicator 29 is configured similar to a dial with angular steps of 1 to 12. In other words, the orientation indicator 29 indicates the orientation in categories. Naturally, it is also possible to use other types of indicators, such as an indicator that indicates the orientation as an angular value. The purpose of the orientation indicators 19 and 29 is to provide a user with an information that corresponds to the determined offset. This information may then be taken into account for selecting an appropriate configuration for a joint implant component.

The exemplary offset adjusted and displayed in FIG. 2 is a distance A of 6 mm and an orientation α of 12 or 0. In the example of FIG. 3, a distance A of 0 mm and an orientation α of 3 has been adjusted. The orientations as angular values illustrated in FIG. 2 and FIG. 3 relative to the reference portion 2 are basically 0° and 90°, respectively.

As already described above, the order of the adjustment devices 10 and 20 may also be reversed. In other words, the second adjustment device 20 may be connected to the reference portion 2, the first adjustment device 10 may be connected to the second adjustment device 20 and the adjustment portion 4 may be connected to the first adjustment device 10. Accordingly, the second adjustment device 20 is for adjusting the orientation angle α relative to the reference portion 2, thereby rotating the first adjustment device 10 by this orientation angle α. This results in the adjustment of the distance A via the first adjustment device 10 being carried out in the direction of the previously adjusted orientation angle α.

In the following, the first adjustment device 10 and the second adjustment device 20 are described in more detail with reference to FIGS. 1 to 4. As illustrated in these figures, the first adjustment device 10 is attached to the reference portion 2. The first adjustment device 10 is configured as an elastic arm latch mechanism 11 for adjusting the distance A.

As already mentioned above, the engagement positions of the elastic arm latch mechanism 11 may be configured on the basis of the variants of a joint implant component and/or its subcomponents. A similar arrangement may be provided for the snap body latch mechanism 21, which is described in more detail below in relation to the second adjustment device 20. This has the advantage that the indicators 19 and 29 may allow for a direct identification of a suitable joint implant component and/or its subcomponents.

In addition, the use of a latch mechanism has the advantage that an adjustment device 10 or 20 is kept at or locked in a position that has been adjusted by a user. In other words, the latch mechanism may prevent an unintentional adjustment of one of the adjustment devices 10 and 20 while, for example, the other one of the adjustment devices 10 and 20 is adjusted. Another advantage of a latch mechanism is that it facilitates a preparation of the implantation site for accommodating the joint implant component after an offset has been selected.

As particularly illustrated in FIG. 4, the first adjustment device 10 has a first body 12 and a second body 13. The first body 12 is configured to pivot about a pivot axis 17 relative to a second body 13. The elastic arm latch mechanism 11 acts between the first body 12 and the second body 13.

In the exemplary embodiment shown in the figures, an elastic arm 14 is preferably integrally provided to the first body 12. The elastic arm 14 comprises a latching member 15. The latching member 15 is configured so that it may reversibly engage with at least one of the engagement members 16. As described above, the engagement members 16 are provided at different positions at the second body 13. The latching member 15 and the engagement members 16 are preferably configured as male and female elements or vice versa. It is also possible to provide several latching members 15 on the elastic arm 14, each of which may be brought into engagement with one engagement member 16 of the second body 13. As an alternative to the illustrated and exemplary embodiment, the elastic arm 14 may be provided to the second body 13.

As illustrated in the figures, the elastic arm 14 may have an actuation portion 18 (see FIGS. 1 and 4). The actuation portion 18 is arranged and configured so that it may be actuated, for example, by a finger of a user. The actuation portion facilitates the operation of the elastic arm latch mechanism, in particular the engagement and disengagement of the latching member 15.

The second body 13 has multiple engagement members 16. In this exemplary case, three engagement members 16 are provided that correspond to 3 different distances (e.g. 0 mm, 3 mm and 6 mm). Naturally, other and/or a different number of distances or adjustment levels may be provided. For example, the second body 13 may include 2, 3, 4, 5, 6, 7 or 8 engagement members 16. The engagement members 16 and or the latching members are preferably integrally formed.

The first body 12 is pivotable so that the latching member of the elastic arm 14 may engage any one of engagement members 16. In the exemplary embodiment illustrated in the figures, engagement is performed by the elastic arm 14 with its latching member 15 being rotated past or in between the engagement members 16 of the second body 13 about the axis of rotation 17.

The distance A of the first adjustment device 10 is adjusted as described above by pivoting the first body 12 about the pivot axis 17. Accordingly, the distances defined by the engagement positions between the latching member 15 and the engagement members 16 do not lie on a straight line. In other words, they are not arranged linearly but on an arc-shaped line. However, the engagement positions are provided on such a short segment of the arc that they may essentially be regarded as lying on a line.

As described above, the engagement positions are preferably distributed along an arc segment of about 40° and preferably about 35°. The accuracy in terms of linearity of the first adjustment device 10 when setting the distance A has been found to be sufficiently precise for the implantation of a joint implant component. At the same time, this configuration of an adjustment device has the advantage that it is robust, easy to assemble, easy to dismantle and easy to clean and disinfect.

In the exemplary embodiment, the second body 13 of the first adjustment device 10 is fixed to the second adjustment device 20. As shown, it is preferably attached to the inner body 24 of the second adjustment device 20, which will be described in more detail below. This fixed connection is preferably established integrally forming the second body 13 with a part of the second adjustment device 20, such as the inner body 24 or the outer body 23 described in the following.

The second adjustment device 20 further comprises an outer body 23, wherein at least a portion of the inner body 24 is received in the outer body 23 so that the inner body 24 and the outer body 23 are rotatable relative to each other. The rotation of the inner body 24 and the outer body 23 relative to each other is preferably facilitated or performed using a rotary actuation portion **24*a*. This actuation portion 24*a* is provided in the illustrated exemplary embodiment at an exposed portion of the inner body 24, i.e. a portion protruding from the outer body 23. Alternatively or additionally, the actuation portion 24*a* of the second adjustment device 20 may be provided on the outer body 23**.

The actuation portion **24*a* may be used during an adjustment of the first adjustment device 10 and an adjustment of the second adjustment device 20. It may also facilitate holding and handling the offset selector 1**.

The adjustment of the orientation angle $\alpha$ is carried out via the relative rotation of the outer body 23 and the inner body 24. As shown in FIG. 4, the outer body 23 may be fixedly connected to the adjustment portion 4.

Similar to the first adjustment device, the second adjustment device 20 preferably comprises a latch mechanism which, in the illustrated exemplary embodiment, is configured as a snap body latch mechanism 21. The function and structure of this snap body latch mechanism 21 will be described in further detail below. In another embodiment, the first adjustment device 10 may (also) be configured as a snap body latch mechanism 21 and/or the second adjustment device 20 may be configured as an elastic arm latch mechanism 11.

The snap body latch mechanism 21 preferably comprises two radially biased snap bodies 22 which are arranged at least partially between the inner circumference of the outer body 23 and the outer circumference of the inner body 24. As mentioned above, the snap bodies 22 are preferably formed as rotary bodies and more preferably as spheres. Thus, they act like a rolling bearing between the inner body 24 and the outer body 23. Accordingly, they may support the relative rotation of the inner body 24 and the outer body 23 relative to each other.

As in the case of the preferred embodiment, the snap bodies 22 are elastically biased radially outwards (i.e. they exert a force outwards) and the outer body 23 has snap recesses 25 for a reversible engagement of the snap bodies 22. During a relative rotation between the inner body 24 and the outer body 23, the relative position of the snap bodies 22 along the circumference of the inner body 24 is fixed. Thus, a relative rotation causes a relative movement of the snap bodies 22 along the inner circumference of the outer body 23. Since the outer body 23 comprises the snap recesses 25 at the level of the snap bodies 22 and the snap bodies 22 are biased radially outwards, this relative movement causes an engagement and disengagement of the snap bodies 22 with each of the snap recesses 25. This provides a user with tactile and/or audible feedback. Similar to the distance indicator 19, the arrangement of the snap recesses 25 also preferably correlates with the orientation indicator 29.

The snap recesses 25 are preferably configured as through-holes extending through the wall of the outer body 23. On the one hand, this has the advantage that a correct assembly of the second adjustment device 20 may simply be checked visually and, on the other hand, the through holes facilitate cleaning the offset selector 1. A cleaning fluid may pass through the snap recesses 25 to the inside and transport residues to the outside. For this function, the outer body 23 or the inner body 24 may also or alternatively comprise through-holes 23*a* (not shown).

Preferably, the snap bodies 22 are each guided in the inner body 24 in a snap body receiving recess 28 so that they may move in a radial direction outwards and inwards during engagement and disengagement, respectively. By guidance of the snap body receiving recesses 28, it is possible to apply the biasing force in a particular defined manner.

In the exemplary embodiment, the biasing force is transferred from an elastic insert 26 to the snap bodies 22. The elastic insert 26 is configured to at least extend over half of the inner circumference of the inner body 24. This allows a single elastic insert 26 to provide a biasing force to multiple snap bodies 22, i.e. two in the illustrated embodiment. For an easier assembly and a more stable arrangement of the elastic insert 26 and, thus, a more precise application of the biasing force, the elastic insert is preferably accommodated in a recess on the inside of the inner body 24 (not shown).

For a defined application of the biasing force, the elastic insert 26 on the side facing a snap body 22 preferably has a snap body receptacle (not shown) which holds a snap body 22 in place relative to the elastic insert 26. Preferably, the snap body receptacles are arranged at the two ends of the elastic insert 26 in order be arranged like the snap bodies 22. The snap body receptacles are preferably configured as a recess or a through holes. If configured as a through hole, the dimension of the through hole is smaller than the cross-section of the snap body. In an assembled state, the elastic insert 26 presses the snap bodies 22 radially outwards via the snap body receptacles of the elastic insert 26.

The preferably U-shaped elastic insert 26 is arranged in a recess on the inner circumference of the inner body 24. The snap bodies 22 are guided by (along) the snap body recesses 28. The snap recesses 22 are configured as through holes and are dimensioned to allow a radial movement of the snap bodies 22. They are arranged to interact with the snap bodies, i.e. they are preferably formed diametrically opposite in the circumferential wall of the inner body 24.

The snap bodies 22 are arranged in the snap body recesses 28 so that they project beyond the outer circumference of the inner body 24. As a result, they are arranged to be moved or pressed into and engaged with the snap recesses 25 by the radial biasing force of the elastic insert 26. If the inner body 24 and the outer body 23 are rotated relative to each other about the offset rotary axis VA, the snap bodies 22 move along the inner circumference of the outer body 23 and thereby repeatedly engage and disengage with the circumferentially arranged snap recesses 25.

It should be noted that the inner body 24, in its longitudinal direction, is hollow inside, i.e. it is configured as a through hole. As shown in FIG. 4, the aforementioned elastic insert 26 and the reference portion 2 may be arranged in this through hole.

The reference portion 2 of the illustrated embodiment is tubular and extends in the longitudinal direction (i.e. in the direction of the offset rotary axis VA) essentially through the offset selector 1. Thus, the offset selector 1 may be placed onto a tool interface using the cavity of the reference portion 2.

After the offset selector 1 has been arranged at and has preferably been engaged with a tool interface, the first adjustment device 10 may in a next step be adjusted to a desired distance A by pivoting the first body 12 and the second body 13 relative to each other. The pivoting action is preferably performed via an actuation portion 18 of an elastic arm 14.

The distance A corresponds to or simulates the distance between an anchoring section and a joint section of a joint implant component. It preferably lies in an offset plane which, as already mentioned above, is essentially perpendicular to the offset rotary axis VA. A predetermined distance A is considered as being adjusted when a latching member 15 of the elastic arm 14 is brought into engagement with a corresponding engagement member 16 of the second body 13.

Further, an orientation angle $\alpha$ of the offset between the reference portion 2 and the adjustment portion 4 may be adjusted preferably subsequently using the second adjustment device 20, i.e. by a rotation of the outer body 23 and the inner body 24 relative to each other. The orientation angle $\alpha$ corresponds to a relative orientation between the anchoring section and the joint section of a joint implant component. Here, adjustment is considered as an engagement of the snap bodies 22 with corresponding snap recesses 25, which reversibly locks the adjustment of the second adjustment means 20.

The adjusted and, thus, determined offset between the reference portion 2 and the adjustment portion 4 may then be identified by a user as a distance A taken from a distance indicator 19 and an orientation $\alpha$ from a orientation indicator 29. These values may then be used to select a suitable joint implant component with an appropriate offset that serves both the anchorage and joint function in the anatomical environment of a patient.

REFERENCE SIGNS

- 1 offset selector
- 2 reference portion
- 3 tool recess
- 4 adjustment portion
- 5 coupling interface
- 10 first adjustment device for an adjustment of the distance
- 11 elastic latch mechanism (Elastic arm latch mechanism)
- 12 first body
- 13 second body
- 14 elastic arm
- 15 latching member
- 16 engagement member
- 17 pivot axis
- 18 actuation portion for adjusting and engaging the latching member
- 19 distance indicator
- 20 second adjustment device for an adjustment of the orientation

21 snap body latch mechanism
22 snap or indexing body
23 outer body
23*a* through hole
24 inner body
24*a* rotary actuation portion
25 snap recess for an engagement with the snap body
26 elastic insert
28 snap body receiving recess
29 orientation indicator
A distance
R reference point
V adjustment point
VA offset rotary axis
α orientation

The invention claimed is:

1. An offset selector for determining an offset between an anchoring section and a joint section of a joint implant component, the offset being defined by a distance and an orientation, the selector comprising:

a reference portion for determining the offset, wherein the reference portion comprises a tool interface configured to engage a tool, a first adjustment device to adjust the distance, wherein the first adjustment device comprises two bodies movable in relation to each other, wherein the first body is mounted to a pivot axis for being pivotable relative to the second body, and wherein a central axis of the tool interface is offset from the pivot axis, and a second adjustment device to adjust the orientation relative to the reference portion, wherein the first adjustment device and the second adjustment device are coupled to each other, one of the first adjustment device and the second adjustment device is connected to the reference portion and the other one of the first adjustment device and the second adjustment device is connected to an adjustment portion, the adjustment portion being movable relative to the reference portion by the distance adjustable via the first adjustment device or by the orientation adjustable via the second adjustment device.

2. The offset selector according to claim 1, wherein the first adjustment device is connected to the reference portion and the second adjustment device is connected to the adjustment portion.

3. The offset selector of claim 1, wherein the tool interface is a through hole having a length greater than a maximum width of a cross-section of the tool interface.

4. The offset selector of claim 1, wherein the reference portion is formed as a recess, having a length which is at least a maximum width of the recess.

5. The offset selector of claim 1, wherein the adjustment portion comprises a coupling interface for being coupled to a tool in at least two positions or orientations.

6. The offset selector of claim 1, wherein the first adjustment device or the second adjustment device comprises a latch mechanism which is adapted to adjust a distance or an orientation in steps.

7. The offset selector of claim 6, wherein the latch mechanism is a snap body latch mechanism comprising at least two snap bodies, each of the snap bodies acting between an outer body and an inner body and being biased in a radial direction, wherein the inner body is rotatably arranged in the outer body and one of the inner and outer bodies comprises a plurality of snap recesses, the snap bodies being reversibly engageable with the snap recesses.

8. The offset selector of claim 7, wherein the snap bodies are biased by an elastic insert, the elastic insert arranged in a recess in an inner side of the inner body.

9. The offset selector of claim 8, wherein the elastic insert has, in at least one end region in a longitudinal direction, a snap body receiving recess for partially receiving one of the snap bodies.

10. The offset selector of claim 6, wherein the latch mechanism comprises an elastic latch mechanism including an elastic arm, the elastic arm being connected to a first of the two bodies and comprising a latching member engageable with an engagement member, wherein the second body comprises a plurality of said engagement members.

11. The offset selector of claim 10, wherein a distance between the pivot axis and an engagement location between the latching member and the engagement member is at least 5 mm.

12. The offset selector of claim 10, wherein the elastic arm has an actuation portion for disengaging the latching member of the elastic arm.

13. The offset selector according to claim 10, wherein the engagement members are arranged over an angular range of at maximum 40°.

14. The offset selector of claim 1, wherein the first adjustment device or the second adjustment device comprises an indicator for indicating the distance or the orientation of the offset.

15. A method for adjusting an offset between an anchoring section and a joint section of a joint implant component using an offset selector according to claim 1, wherein the offset is defined by a distance and an orientation and wherein the method comprises the steps:

bringing a reference portion of the offset selector in contact with a first tool for preparing an anchoring recess in bone tissue of a patient;

bringing a second tool into engagement with an adjustment portion of the offset selector;

adjusting the distance between the reference portion and the adjustment portion via the first adjustment device;

adjusting the orientation between the reference portion and the adjustment portion via the second adjustment device;

wherein the reference portion and the adjustment portion are coupled in series via the first adjustment device and the second adjustment device.

16. The offset selector according to claim 1, wherein the first adjustment device is configured as an elastic arm latch mechanism, and wherein the elastic arm is integrally formed with the first body.

17. The offset selector according to claim 1, wherein the reference portion is configured as a through hole extending through the offset selector, and wherein the through hole is adapted to receive a tool interface of a reamer.

18. The offset selector according to claim 1, wherein the second adjustment device comprises an inner body and an outer body rotatable relative to each other, and wherein the inner body is hollow and configured to receive the reference portion therein.

19. The offset selector according to claim 1, wherein the adjustment portion comprises a coupling interface having indications for coupling a tool in different orientations corresponding to left and right sides of a patient.

20. The offset selector according to claim 1, wherein the second adjustment device comprises snap bodies formed as spheres acting as a rolling bearing between an inner body and an outer body.

* * * * *